(12) United States Patent
Miyaji et al.

(10) Patent No.: US 7,799,939 B2
(45) Date of Patent: Sep. 21, 2010

(54) PROCESS FOR PRODUCTION OF DIALKYL CARBONATE AND DIOL

(75) Inventors: Hironori Miyaji, Tokyo (JP); Shinsuke Fukuoka, Tokyo (JP); Hiroshi Hachiya, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 182 days.

(21) Appl. No.: 11/990,913

(22) PCT Filed: Sep. 5, 2006

(86) PCT No.: PCT/JP2006/317492

§ 371 (c)(1), (2), (4) Date: Sep. 2, 2008

(87) PCT Pub. No.: WO2007/034669

PCT Pub. Date: Mar. 29, 2007

(65) Prior Publication Data

US 2009/0149669 A1 Jun. 11, 2009

(30) Foreign Application Priority Data

Sep. 20, 2005 (JP) ............................. 2005-272557

(51) Int. Cl.
C07C 68/06 (2006.01)

(52) U.S. Cl. ..................................... 558/277

(58) Field of Classification Search ............... None
See application file for complete search history.

(56) References Cited

U.S. PATENT DOCUMENTS

| | | |
|---|---|---|
| 3,642,858 A | 2/1972 | Frevel et al. |
| 3,803,201 A | 4/1974 | Gilpin et al. |
| 4,062,884 A | 12/1977 | Romano et al. |
| 4,181,676 A | 1/1980 | Buysch et al. |
| 4,307,032 A | 12/1981 | Krimm et al. |
| 4,661,609 A | 4/1987 | Knifton |
| 4,691,041 A | 9/1987 | Duranleau et al. |
| 4,734,518 A | 3/1988 | Knifton |
| 5,231,212 A | 7/1993 | Buysch et al. |
| 5,359,118 A | 10/1994 | Wagner et al. |
| 6,346,638 B1 | 2/2002 | Tojo et al. |
| 6,479,689 B1 | 11/2002 | Tojo et al. |

FOREIGN PATENT DOCUMENTS

| | | |
|---|---|---|
| DE | 4129316 A1 | 9/1991 |
| DE | 4216121 A1 | 5/1992 |
| EP | 1086940 A1 | 3/2001 |
| EP | 1174406 A1 | 1/2002 |
| JP | 51-122025 | 10/1976 |
| JP | 54-48715 A | 4/1979 |
| JP | 54-48716 A | 4/1979 |
| JP | 54-063023 A | 5/1979 |
| JP | 54-148726 A | 11/1979 |
| JP | 55-064550 A | 5/1980 |
| JP | 55-064551 A | 5/1980 |
| JP | 56-010144 A | 2/1981 |
| JP | 63-41432 A | 2/1988 |
| JP | 63-238043 A | 10/1988 |
| JP | 64-31737 A | 2/1989 |
| JP | 5-213830 A | 8/1993 |
| JP | 6-9507 A | 1/1994 |
| JP | 2002-308804 A | 10/2002 |
| JP | 2002-371037 A | 12/2002 |
| JP | 2004-131394 A | 4/2004 |
| JP | 04-198141 A | 7/2004 |
| JP | 2004-198141 A | 7/2004 |
| JP | 04-230243 A | 8/2004 |
| JP | 2004-230243 A | 8/2004 |
| WO | WO-97/23445 | 7/1997 |
| WO | WO 97/23445 | 7/1997 |
| WO | WO-99/64382 | 12/1999 |
| WO | WO-00/51954 | 9/2000 |

*Primary Examiner*—Kamal A Saeed
(74) *Attorney, Agent, or Firm*—Birch, Stewart, Kolasch & Birch, LLP

(57) ABSTRACT

It is an object of the present invention to provide, for a case of producing a dialkyl carbonate and a diol from a cyclic carbonate and an aliphatic monohydric alcohol, a process that simultaneously satisfies the cyclic carbonate conversion being high, the selectivities for the dialkyl carbonate and diol to be produced being high, and a high-purity diol having a high UV transmittance and a low aldehyde content being obtained without carrying out complicated treatment such as feeding water into a diol distillation purification step. The present invention discloses a process for the production of the dialkyl carbonate and the diol in which, when producing the dialkyl carbonate and the diol by reacting the cyclic carbonate and the aliphatic monohydric alcohol together in the presence of a catalyst in a transesterification reactor comprising a tray type continuous multi-stage distillation column, reaction conditions (residence times, temperatures) in the distillation column are controlled to be specific conditions.

4 Claims, 1 Drawing Sheet

PROCESS FOR PRODUCTION OF DIALKYL CARBONATE AND DIOL

TECHNICAL FIELD

The present invention relates to a process for the production of a dialkyl carbonate and a diol by reacting a cyclic carbonate and an aliphatic monohydric alcohol together.

DESCRIPTION OF THE RELATED ART

Several processes for the production of a dialkyl carbonate and a diol from a reaction between a cyclic carbonate and an aliphatic monohydric alcohol have been proposed, with four systems having been proposed hitherto as reaction systems. These four reaction systems are used in a process for the production of dimethyl carbonate and ethylene glycol from ethylene carbonate and methanol, which is the most typical reaction example.

A first system is a completely batch reaction system in which ethylene carbonate, methanol and a catalyst are put into an autoclave to proceed the reaction, which is a batch reaction vessel (see, for example, Patent Document 1: U.S. Pat. No. 3,642,858, Patent Document 2: Japanese Patent Application Laid-Open No. 54-48715 (corresponding to U.S. Pat. No. 4,181,676), Patent Document 5: Japanese Patent Application Laid-Open No. 54-63023, Patent Document 6: Japanese Patent Application Laid-Open No. 54-148726, Patent Document 7: Japanese Patent Application Laid-Open No. 55-64550, Patent Document 8: Japanese Patent Application Laid-Open No. 55-64551, Patent Document 9: Japanese Patent Application Laid-Open No. 56-10144).

A second system is a batch reaction system having a distillation column, which uses an apparatus in which a distillation column is provided on a top of a reaction vessel, and in which ethylene carbonate, methanol and a catalyst are fed into the reaction vessel, and reaction is made to proceed by heating to a predetermined temperature (see, for example, Patent Document 3: Japanese Patent Application Laid-Open No. 51-122025 (corresponding to U.S. Pat. No. 4,062,884), Patent Document 4: Japanese Patent Application Laid-Open No. 5448716 (corresponding to U.S. Pat. No. 4,307,032), Patent Document 14: U.S. Pat. No. 3,803,201).

A third system is a continuous flow reaction system in which a mixed solution of ethylene carbonate and methanol is continuously fed into a tubular reactor maintained at a predetermined reaction temperature, and a reaction mixture containing unreacted ethylene carbonate, unreacted methanol, produced dimethyl carbonate, and produced ethylene glycol is continuously withdrawn in a liquid form from an outlet on the other side (see, for example, Patent Document 10: Japanese Patent Application Laid-Open No. 6341432 (corresponding to U.S. Pat. No. 4,661,609), Patent Document 11: Japanese Patent Application Laid-Open No. 63-238043, Patent Document 12: Japanese Patent Application Laid-Open No. 64-31737 (corresponding to U.S. Pat. No. 4,691,041), Patent Document 13: U.S. Pat. No. 4,734,518).

A fourth system is a reactive distillation system, i.e. a continuous production process in which ethylene carbonate and methanol are each continuously fed into a multi-stage distillation column, and reaction is carried out in the presence of a catalyst in a plurality of stages in the distillation column, while the separation of produced dimethyl carbonate and ethylene glycol is carried out in the same distillation column simultaneously (see, for example, Patent Document 15: Japanese Patent Application Laid-Open No. 4-198141, Patent Document 16: Japanese Patent Application Laid-Open No. 4-230243, Patent Document 17: Japanese Patent Application Laid-Open No. 5-213830 (corresponding to German Patent No. 4,129,316), Patent Document 18: Japanese Patent Application Laid-Open No. 6-9507 (corresponding to German Patent No. 4,216,121)).

In this way, the processes proposed hitherto for producing the dialkyl carbonate and the diol from the cyclic carbonate and the aliphatic monohydric alcohol are the four systems:
(1) the completely batch reaction system;
(2) the batch reaction system using the reaction vessel having the distillation column provided on the top thereof;
(3) a flowing liquid reaction system using the tubular reactor; and
(4) the reactive distillation system.

However, problems have been pointed out for these as follows.

In the case of (1) and (3), the upper limit of the cyclic carbonate conversion is determined by the composition put in and the temperature, and hence, the reaction cannot be carried out to completion. Thus, the conversion is low, because this reaction is an equilibrium reaction with a low equilibrium constant. Moreover, in the case of (2), to make the cyclic carbonate conversion high, a very large amount of the aliphatic monohydric alcohol must be used. In the case of (4), the reaction can be made to proceed with a higher conversion than with (1), (2) or (3), and hence this is the best reaction. For example, in Example 1 in Patent Document 15 (Japanese Patent Application Laid-Open No. 4-198141), the ethylene carbonate conversion is 100%, and the ethylene glycol reaction yield and selectivity are 99.5%. Moreover, in Example 1 in Patent Document 16 (Japanese Patent Application Laid-Open No. 4-230243), the ethylene carbonate conversion is 100%, and the ethylene glycol reaction yield and selectivity are 99.4%. In this way, with the reactive distillation system (4), a high conversion and a high selectivity are exhibited. Furthermore, to cope with the case that a small amount of unreacted cyclic carbonate remains in the produced diol, there have also been proposed a process in which the unreacted cyclic carbonate is hydrolyzed (see, for example, Patent Document 19: International Publication No. 97/23445), and a process in which the unreacted cyclic carbonate is converted into an ether through reaction with the diol (see, for example, Patent Document 20: International Publication No. 00/51954).

However, while studying the reactive distillation system proposed hitherto, a new problem has been discovered in that the diol produced has a low ultra violet light (hereinafter abbreviated to "UV") transmittance at a certain wavelength, and contains an aldehyde compound. With regard to this problem, there has been proposed a process in which a high-purity diol having a high UV transmittance and a low aldehyde content is obtained by feeding specified water into a diol distillation purification step (see, for example, Patent Document 21: Japanese Patent Application Laid-Open No. 2002-308804, Patent Document 22: Japanese Patent Application Laid-Open No. 2004-131394). However, with this system, because water is fed into the diol distillation purification step, there is a problem that the process becomes complicated. Further improvement is thus required.

For the case of producing the dialkyl carbonate and the diol from the cyclic carbonate and the aliphatic monohydric alcohol, up to now there has not been proposed a process that simultaneously satisfies the cyclic carbonate conversion being high, the selectivities for the dialkyl carbonate and diol to be produced being high, and a high-purity diol having a high UV transmittance and a low aldehyde content being obtained without carrying out complicated treatment such as feeding water into a diol distillation purification step.

DISCLOSURE OF INVENTION

Problem to be Solved by the Invention

It is an object of the present invention to provide, for a case of producing a dialkyl carbonate and a diol from a cyclic carbonate and an aliphatic monohydric alcohol, a process that simultaneously satisfies the cyclic carbonate conversion being high, the selectivities for the dialkyl carbonate and diol to be produced being high, and a high-purity diol having a high UV transmittance and a low aldehyde content being obtained without carrying out complicated treatment such as feeding water into a diol distillation purification step.

Means for Solving the Problem

The present inventors have carried out assiduous studies focusing on the mechanism of a reaction in which material such as an aldehyde that reduces the UV transmittance of a diol is produced, and as a result have reached to the present invention after discovering that the reaction conditions (residence time, temperature) in a transesterification reactor comprising a tray column type continuous multi-stage distillation column play an important influence on the reaction producing UV transmittance-reducing material, and moreover that this influence differs between a tray portion and a column bottom portion.

That is, the present invention provides:
1. In a process for continuous production of a dialkyl carbonate and a diol, by continuously feeding a first starting material containing a cyclic carbonate as a main component thereof and a second starting material containing an aliphatic monohydric alcohol as a main component thereof into a tray column type continuous multi-stage distillation column, bringing the starting materials into contact with a catalyst present in said distillation column so as to bring about reaction in a tray portion and a column bottom portion, continuously withdrawing a low boiling point component containing a produced dialkyl carbonate from an upper portion of said distillation column, and continuously withdrawing a high boiling point component containing a produced diol from a lower portion of said distillation column, wherein the improvement comprises:
the following formula (I) being satisfied, $$780 \leq \alpha + 1.24 \times \beta \leq 5150 \quad (1),$$

wherein
$\alpha = \theta_1^{0.52} \times (T_1 + 120)^{1.2}$,
$\beta = \theta_2^{0.52} \times (T_2 + 120)^{1.2}$,
$\theta_1$ (hours) is an average residence time of the reaction liquid in the tray portion of said distillation column in which the catalyst is present;
$T_1$ (° C.) is a temperature at a $(n/2)^{th}$ stage (a $((n+1)/2)^{th}$ stage in the case that n is odd) from the top of the tray portion in which the catalyst is present wherein n is a total number of stages therein;
$\theta_2$ (hours) is an average residence time of the reaction liquid in the column bottom portion of said distillation column; and
$T_2$ (° C.) is a temperature in the column bottom portion,
2. the process for continuous production of the dialkyl carbonate and the diol according to item 1, wherein the catalyst is a homogeneous catalyst,
3. the process for continuous production of the dialkyl carbonate and the diol according to item 1 or 2, wherein $\theta_1$ is in a range of from 0.3 to 20 hours, and $\theta_2$ is in a range of from 0.3 to 25 hours,
4. the process for continuous production of the dialkyl carbonate and the diol according to any one of items 1 to 3, wherein each of $T_1$ and $T_2$ is in a range of from −20° C. to 350° C.

Advantageous Effects Of The Invention

According to the process of the present invention, when producing the dialkyl carbonate and the diol from the cyclic carbonate and the aliphatic monohydric alcohol, there can be simultaneously satisfied the cyclic carbonate conversion being high, the selectivities for the dialkyl carbonate and diol to be produced being high, and a high-purity diol having a high UV transmittance and a low aldehyde content being obtained without carrying out complicated treatment such as feeding water into a diol distillation purification step.

Figure 1:
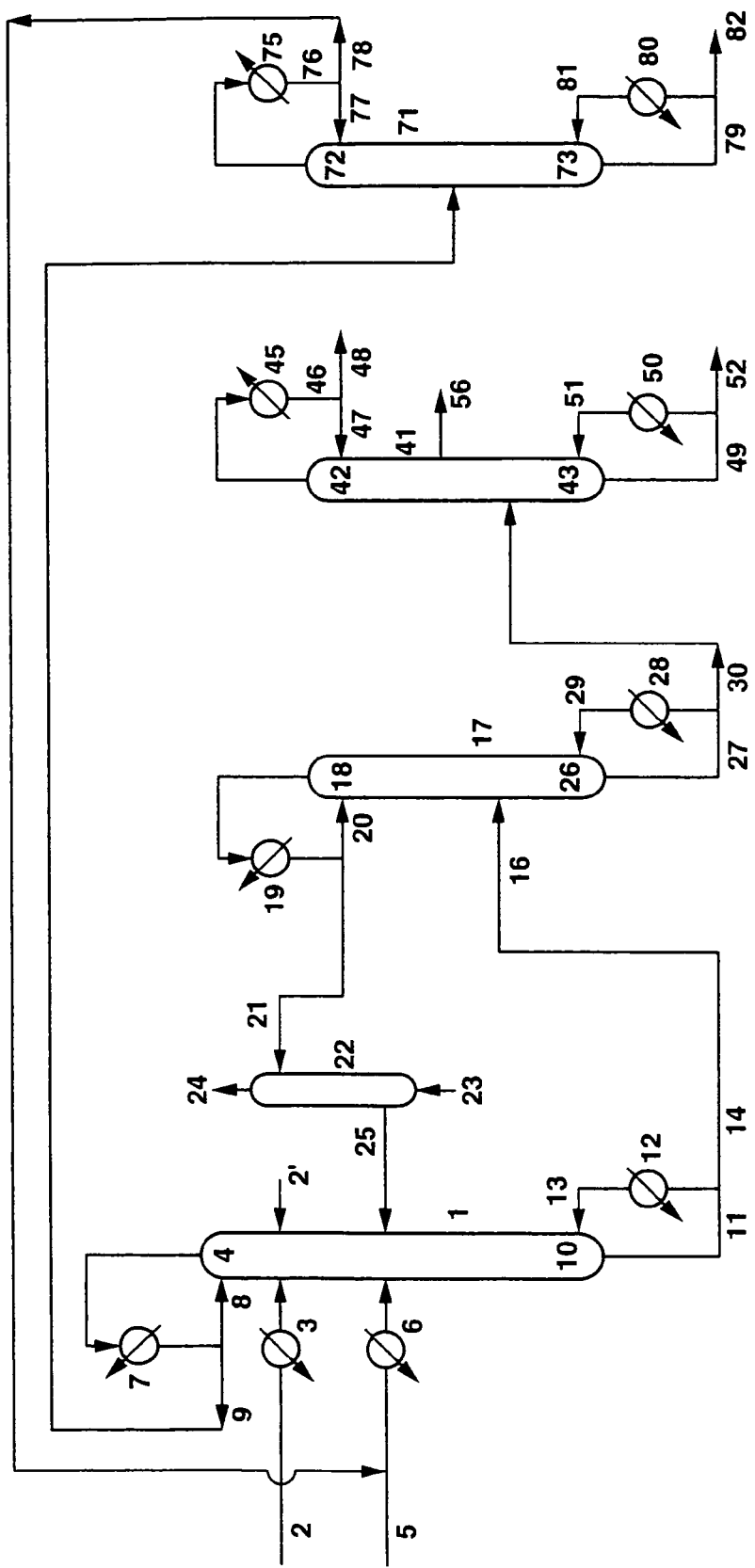
FIG. 1 is a schematic drawing of an apparatus used in Examples according to the present invention and Comparative Examples.

1: continuous multi-stage distillation column; 3, 6: preheater; 4, 18, 42, 72: top of column; 7, 19, 45, 75: condenser; 10, 26, 43, 73: column bottom; 12, 28, 50, 80: reboiler; 17: low boiling point component separating column; 22: carbon dioxide-eliminating column; 41: EG purifying column; 71: DMC separating column; 2, 2', 5, 8, 9, 11, 13, 14, 16, 20, 21, 23, 24, 25, 27, 29, 30, 46, 47, 48, 49, 51, 52, 56, 76, 77, 78, 79, 81, 82: conduit

BEST MODE FOR CARRYING OUT THE INVENTION

Following is a detailed description of the present invention.
The reaction of the present invention is a reversible equilibrium transesterification reaction represented by following general formula (I) in which dialkyl carbonates (C) and diols (D) are produced from cyclic carbonates (A) and aliphatic monohydric alcohols (B).

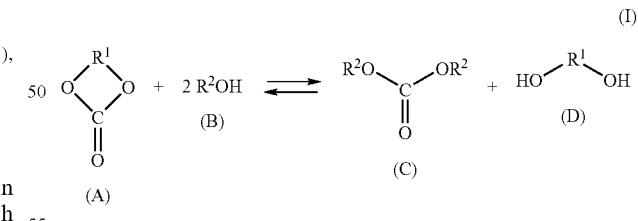

(I)

[wherein $R^1$ represents a bivalent group —$(CH_2)_m$— (m is an integer from 2 to 6), one or more of the hydrogens thereof being optionally substituted with an alkyl group or aryl group having 1 to 10 carbon atoms. Moreover, $R^2$ represents a monovalent aliphatic group having 1 to 12 carbon atoms, one or more of the hydrogens thereof being optionally substituted with an alkyl group or aryl group having 1 to 10 carbon atoms.]

In the present invention, UV transmittance-reducing material in the diol is a trace component that has not been fully identified, but it is thought that aldehyde (E) is produced from the diol (D) through an irreversible dehydration reaction represented by following general formula (II).

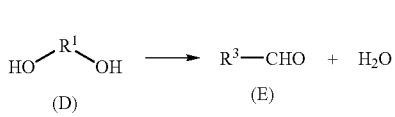

[wherein, $R^3$ represents a monovalent group $CH_3$—$(CH_2)_{m-2}$— (m is an integer from 2 to 6), one or more of the hydrogens thereof being optionally substituted with an alkyl group or aryl group having 1 to 10 carbon atoms.]

It is thought that this aldehyde (E) and material produced through further reaction of the aldehyde (E) form the UV transmittance-reducing material.

The reason why, in the present invention, it is possible to simultaneously satisfy the cyclic carbonate conversion being high, the selectivities for the dialkyl carbonate and diol to be produced being high, and the high-purity diol having the high UV transmittance and the low aldehyde content being obtained without carrying out complicated treatment such as feeding water into the diol distillation purification step is not clear, but is thought to be as follows.

The above reaction (II) is a first-order dehydration reaction of the diol, and it is thought that the residence time and the temperature greatly affect the reaction, the reaction proceeding more the greater the residence time or the temperature. In particular, it is thought that the reason that the order for the temperature is higher than that for the residence time for each of α and β in formula (1) in the present invention is that the temperature dependence of above reaction (II) is greater than the residence time dependence. Moreover, in the transesterification reactor comprising the tray column type continuous multi-stage distillation column, the diol in the high boiling point component is withdrawn from a lower portion of the column, and hence it is thought that the diol concentration is higher in the column bottom portion than in the tray portion, and thus the contribution to aldehyde production from the reaction mechanism of above reaction (II) is greater for the column bottom portion, and hence the coefficient for β in formula (1) in the present invention is greater than for α.

In the present invention, if the value of α+1.24×β in formula (1) is greater than 5150, then the produced diol has a low UV transmittance and a high aldehyde content, i.e. a low-purity diol is obtained. If the value of α+1.24×β is less than 780, then reaction (I) does not proceed, and hence the cyclic carbonate conversion and the dialkyl carbonate and diol selectivities decrease. Accordingly, as the range in formula (1), the reaction condition 780≦α+1.24×β≦5150 is chosen, preferably 1200≦α+1.24 ×β≦4300, more preferably 1600≦α+1.24×β≦3700.

If the average residence time of the reaction liquid $\theta_1$ (hours) in the tray portion of said distillation column in which the catalyst is present is too long, then reaction (II) proceeds and aldehyde is produced, whereas if $\theta_1$ is too short, then reaction (I) does not proceed and hence the cyclic carbonate conversion and the dialkyl carbonate and diol selectivities decrease; $\theta_1$ is thus generally in a range of from 0.3 to 20 hours, preferably from 0.5 to 10 hours, more preferably from 0.8 to 6 hours. In addition, diol concentration is extremely low in the tray portion in which the catalyst is not present, because reaction (I) does not proceed. Therefore, reaction (II) also does not proceed.

For similar reasons, the average residence time of the reaction liquid $\theta_2$ (hours) in the column bottom portion of said distillation column is generally in a range of from 0.3 to 25 hours, preferably from 0.5 to 16 hours, more preferably from 1.0 to 11 hours.

The temperature $T_1$ (° C.) at the $(n/2)^{th}$ stage (the $((n+1)/2)^{th}$ stage in the case that n is odd) from the top of the tray portion in which the catalyst is present wherein n is a total number of stages therein, and the temperature $T_2$ (° C.) in the column bottom portion vary depending on the types of the starting material compounds used and the reaction pressure, but $T_1$ is generally in a range of from −20 to 350° C., preferably from 0 to 200° C., more preferably from 30 to 170° C., and $T_2$ is generally in a range of from −20 to 350° C., preferably from 10 to 250° C., more preferably from 50 to 220° C. If these temperatures are too high, then reaction (II) proceeds and the aldehyde is produced, whereas if these temperatures are too low, then reaction (I) does not proceed and hence the cyclic carbonate conversion and the dialkyl carbonate and diol selectivities decrease.

Moreover, the operating pressure of said distillation column may be any of a reduced pressure, normal pressure, or an applied pressure, and in terms of absolute pressure is generally in a range of from 1 Pa to $2\times10^6$ Pa, preferably from $1\times10^3$ to $1\times10^6$ Pa, more preferably from $1\times10^4$ to $5\times10^5$ Pa. The operating pressure is generally determined from the composition in said distillation column such that the reaction temperatures $T_1$ and $T_2$ in said distillation column become suitable temperatures.

The form of the transesterification reactor used in the present invention is a tray column type continuous multi-stage distillation column. The term "continuous multi-stage distillation column" refers to a distillation column that has a plurality of, i.e. at least two, distillation stages, and that enables continuous distillation to be carried out. The term "stages" in the present invention refers to the actual number of stages of trays.

As the tray column type continuous multi-stage distillation column, any one generally used as a continuous type tray column type multi-stage distillation column can be used, for example one using trays such as bubble-cap trays, sieve trays, valve trays, or counterflow trays. Moreover, in the case of using a solid catalyst, a tray column type continuous multi-stage distillation column in which this solid catalyst is fixed in the tray stages and the column bottom portion can be used. Moreover, as the continuous multi-stage distillation column used in the present invention, a distillation column as above may be used alone, or a plurality of such distillation columns may be used in combination connected together in series or parallel.

The cyclic carbonate used as a starting material in the present invention is a compound represented by (A) in above reaction formula (I). Examples of the cyclic carbonate include alkylene carbonates such as ethylene carbonate, propylene carbonate, 1,3-dioxacyclohexa-2-one, 1,3-dioxacyclohepta-2-one, or the like, which are preferably used in the present invention, ethylene carbonate or propylene carbonate being more preferably used due to ease of procurement and so on, and ethylene carbonate being particularly preferably used.

Moreover, the aliphatic monohydric alcohol used as the other starting material is a compound represented by (B) in above reaction formula (I). An aliphatic monohydric alcohol having a lower boiling point than the diol produced is used. Although possibly varying depending on the type of the cyclic carbonate used, examples of the aliphatic monohydric alcohol include methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and so on. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e. methanol, ethanol, propanol (isomers), and butanol (isomers). In the case of using ethylene carbonate or propylene carbonate as the cyclic carbonate, preferable aliphatic monohydric alcohols are methanol and ethanol, methanol being particularly preferable.

In the process of the present invention, a catalyst is made to be present in the transesterification reactor. The method of making the catalyst be present may be any method, but in the case, for example, of a homogeneous catalyst that dissolves in the reaction liquid under the reaction conditions, the catalyst can be made to be present in the liquid phase in the transesterification reactor by feeding the catalyst into the transesterification reactor continuously, or in the case of a heterogeneous catalyst that does not dissolve in the reaction liquid under the reaction conditions, the catalyst can be made to be present in the reaction system by disposing the catalyst as a solid in the transesterification reactor; these methods may also be used in combination.

In the case that a homogeneous catalyst is continuously fed into the multi-stage distillation column constituting the transesterification reactor, the homogeneous catalyst may be fed in together with the cyclic carbonate and/or the aliphatic monohydric alcohol, or may be fed in at a different position to the starting materials. The transesterification catalyst may be fed in at any position at least one stage from the bottom of the column. However, the reaction actually proceeds in said distillation column in a region below the position at which the catalyst is fed in, and hence it is preferable to feed said catalyst into a region between the top of the column and the position at which the starting materials are fed in.

Moreover, in the case of using a heterogeneous solid catalyst, said catalyst can be installed in the required amount in any chosen position in the reactor, the number of stages in which said catalyst is present being at least one stage, preferably at least two stages.

In the case of using a heterogeneous solid catalyst, degradation and/or degeneration of the catalyst may occur under prolonged continuous operation, and in such a case it is necessary to replace new solid catalyst. It is thus more preferable to use a homogeneous catalyst.

As the catalyst used in the present invention, any of various catalysts known from hitherto can be used. Examples that can be used include;

alkali metals and alkaline earth metals such as lithium, sodium, potassium, rubidium, cesium, magnesium, calcium, strontium, barium or the like;

basic compounds such as hydrides, hydroxides, alkoxides, aryloxides, amides or the like of alkali metals and alkaline earth metals;

basic compounds such as carbonates, bicarbonates, organic acid salts or the like of alkali metals and alkaline earth metals;

tertiary amines such as triethylamine, tributylamine, trihexylamine, and benzyldiethylamine or the like;

nitrogen-containing heteroaromatic compounds such as N-alkylpyrroles, N-alkylindoles, oxazoles, N-alkylimidazoles, N-alkylpyrazoles, oxadiazoles, pyridine, alkylpyridines, quinoline, alkylquinolines, isoquinoline, alkylisoquinolines, acridine, alkylacridines, phenanthroline, alkylphenanthrolines, pyrimidine, alkylpyrimidines, pyrazine, alkylpyrazines, triazines, alkyltriazines or the like;

cyclic amidines such as diazabicycloundecene (DBU), diazabicyclononene (DBN) or the like;

thallium compounds such as thallium oxide, thallium halides, thallium hydroxide, thallium carbonate, thallium nitrate, thallium sulfate, thallium organic acid salts or the like;

tin compounds such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate or the like;

zinc compounds such as dimethoxyzinc, diethoxyzinc, ethylenedioxyzinc, dibutoxyzinc or the like;

aluminum compounds such as aluminum trimethoxide, aluminum triisopropoxide, aluminum tributoxide or the like;

titanium compounds such as tetramethoxytitanium, tetraethoxytitanium, tetrabutoxytitanium, dichlorodimethoxytitanium, tetraisopropoxytitanium, titanium acetate, titanium acetylacetonate or the like;

phosphorus compounds such as trimethylphosphine, triethylphosphine, tributylphosphine, triphenylphosphine, tributylmethylphosphonium halides, trioctylbutylphosphonium halides, triphenylmethylphosphonium halides or the like;

zirconium compounds such as zirconium halides, zirconium acetylacetonate, zirconium alkoxides, zirconium acetate or the like;

lead and lead-containing compounds, for example lead oxides such as PbO, $PbO_2$, $Pb_3O_2$ or the like; lead sulfides such as PbS, $Pb_2S_3$, $PbS_2$ or the like; lead hydroxides such as $Pb(OH)_2$, $Pb_3O_2(OH)_2$, $Pb_2[PbO_2(OH)_2]$, $Pb_2O(OH)_2$ or the like; plumbites such as $Na_2PbO_2$, $K_2PbO_2$, $NaHPbO_2$, $KHPbO_2$ or the like; plumbates such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$ or the like; lead carbonates and basic salts thereof such as $PbCO_3$, $2PbCO_3.Pb(OH)_2$ or the like; alkoxylead compounds and aryloxylead compounds such as $Pb(OCH_3)_2$, $(CH_3O)Pb(OPh)$, $Pb(OPh)_2$ or the like; lead salts of organic acids, and carbonates and basic salts thereof, such as $Pb(OCOCH_3)_2$, $Pb(OCOCH_3)_4$, $Pb(OCOCH_3)_2.PbO.0.3H_2O$ or the like; organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ or the like (wherein Bu represents a butyl group, and Ph represents a phenyl group); lead alloys such as Pb—Na, Pb—Ca, Pb—Ba, Pb—Sn, Pb—Sb or the like; lead minerals such as galena and zinc blende; and hydrates of such lead compounds;

ion exchangers such as anion exchange resins having tertiary amino groups, ion exchange resins having amide groups, ion exchange resins having at least one type of exchange groups selected from sulfonate groups, carboxylate groups and phosphate groups, and solid strongly basic anion exchangers having quaternary ammonium groups as exchange groups, or the like;

solid inorganic compounds such as silica, silica-alumina, silica-magnesia, aluminosilicates, gallium silicate, various zeolites, various metal-exchanged zeolites, and ammonium-exchanged zeolites, or the like.

As a solid catalyst, a particularly preferably used one is a solid strongly basic anion exchanger having quaternary ammonium groups as exchange groups. Examples thereof include a strongly basic anion exchange resin having quaternary ammonium groups as exchange groups, a cellulose-based strongly basic anion exchanger having quaternary ammonium groups as exchange groups, and an inorganic carrier supported type strongly basic anion exchanger having quaternary ammonium groups as exchange groups. Examples of the strongly basic anion exchange resin having quaternary ammonium groups as exchange groups include a styrene type strongly basic anion exchange resin or the like. The styrene type strongly basic anion exchange resin is a strongly basic anion exchange resin having a copolymer of styrene and divinylbenzene as a parent material, and having quaternary ammonium groups (type I or type II) as exchange groups, and can be schematically represented, for example, by following formula (III).

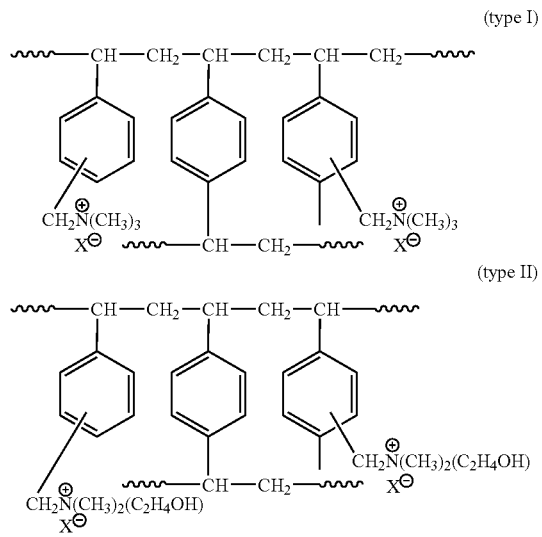

In the above formula, X represents an anion; examples of X generally include at least one type of anion selected from $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$, and $ClO_3^-$, preferably at least one type of anion selected from $Cl^-$, $Br^-$, $HCO_3^-$, and $CO_3^{2-}$. Moreover, examples of the structure of the resin parent material include a gel type one or a macroreticular (MR) type, the MR type being particularly preferable due to the organic solvent resistance being high.

Examples of the cellulose-based strongly basic anion exchanger having quaternary ammonium groups as exchange groups include cellulose having —$OCH_2CH_2NR_3X$ exchange groups obtained by converting some or all of the —OH groups in the cellulose into trialkylaminoethyl groups. Herein, R represents an alkyl group such as methyl, ethyl, propyl, butyl or the like, preferably methyl or ethyl. Moreover, X is defined as above.

The inorganic carrier supported type strongly basic anion exchanger having quaternary ammonium groups as exchange groups that can be used in the present invention means an inorganic carrier that has had —$O(CH_2)_nNR_3X$ quaternary ammonium groups introduced thereto by modifying some or all of the —OH surface hydroxyl groups of the inorganic carrier. Herein, R and X are defined as above, and n is generally an integer from 1 to 6, preferably n=2. Examples of the inorganic carrier include silica, alumina, silica-alumina, titania, zeolite or the like, preferably silica, alumina, or silica-alumina, particularly preferably silica.

Any method can be used as the method of modifying the surface hydroxyl groups of the inorganic carrier. For example, the inorganic carrier and an aminoalcohol HO$(CH_2)_nNR_2$ are made to undergo a dehydration reaction in the presence of a basic catalyst so as to introduce aminoalkoxy groups, and then reaction is carried out with an alkyl halide RX' (X' represents a halogen, Cl, Br, I or the like generally being used) to obtain —$O(CH_2)_nNR_3X'$ groups. Anion exchange is then further carried out, so as to obtain —$O(CH_2)_nNR_3X$ quaternary ammonium groups having the desired anion X. Moreover, in the case that n=2, the inorganic carrier may be treated with an N,N-dialkylaziridine to obtain —$OCH_2CH_2NR_2$ N,N-dialkylaminoethoxy groups, and then —$O(CH_2)_nNR_3X$ groups may be obtained using the above method.

The solid strongly basic anion exchanger having quaternary ammonium groups as exchange groups is commercially available. In this case, the anion exchanger may also be used as the transesterification catalyst after being subjected to ion exchange with a desired anionic species in advance as pretreatment. Moreover, a solid catalyst comprising a macroreticular or gel-type organic polymer having bonded thereto heterocyclic groups each containing at least one nitrogen atom, or an inorganic carrier having bonded thereto heterocyclic groups each containing at least one nitrogen atom can also be preferably used as the transesterification catalyst. Furthermore, a solid catalyst in which some or all of these nitrogen-containing heterocyclic groups have been converted into a quaternary salt can be similarly used.

The amount of the catalyst used in the present invention varies depending on the type of the catalyst used, but in the case of continuously feeding in a homogeneous catalyst that dissolves in the reaction liquid under the reaction conditions, the amount used is generally in a range of from 0.001 to 50% by weight, preferably from 0.001 to 25% by weight, more preferably from 0.005 to 10% by weight, as a proportion of the total weight of the cyclic carbonate and the aliphatic monohydric alcohol fed in as the starting materials. Moreover, in the case of using the solid catalyst installed in said distillation column, the catalyst is preferably used in an amount in a range of from 0.01 to 75 vol %, more preferably from 0.05 to 50 vol %, yet more preferably from 0.1 to 25 vol %, based on the empty column volume of said distillation column.

There are no particular limitations on the method of continuously feeding the cyclic carbonate and the aliphatic monohydric alcohol into the continuous multi-stage distillation column constituting the transesterification reactor; any feeding method may be used so long as the cyclic carbonate and the aliphatic monohydric alcohol can be made to contact the catalyst in a region of at least one stage, preferably at least two stages, of said distillation column. That is, said cyclic carbonate and said aliphatic monohydric alcohol can be continuously fed in from a required number of inlets in stages of the continuous multi-stage distillation column satisfying the conditions described above. Moreover, said cyclic carbonate and said aliphatic monohydric alcohol may be introduced into the same stage of said distillation column, or may be introduced into different stages to one another.

The starting materials may be fed continuously into said distillation column in a liquid form, in a gaseous form, or as a mixture of a liquid and a gas. Other than feeding the starting materials into said distillation column in this way, it is also preferable to additionally feed in a gaseous starting material intermittently or continuously from the lower portion of said distillation column. Moreover, another preferable method is one in which said cyclic carbonate is continuously fed in a liquid form or a gas/liquid mixed form into a stage of said distillation column above the stages in which the catalyst is present, and said aliphatic monohydric alcohol is continuously fed in a gaseous form and/or a liquid form into the lower portion of said distillation column. In this case, the cyclic carbonate may of course contain the aliphatic monohydric alcohol.

In the present invention, the starting materials fed in may contain a small amount of the diol as a product. Moreover, the aliphatic monohydric alcohol used may contain the dialkyl carbonate, the percentage by weight of the dialkyl carbonate in the aliphatic monohydric alcohol/dialkyl carbonate mixture generally being in a range of from 0 to 40% by weight, preferably from 0.1 to 30% by weight, more preferably from 1 to 20% by weight.

The amount ratio between the cyclic carbonate and the aliphatic monohydric alcohol fed into the transesterification reactor varies according to the type and amount of the transesterification catalyst and the reaction conditions, but the molar ratio of the aliphatic monohydric alcohol to the cyclic carbonate fed in is generally in a range of from 0.01 to 1000 times. To increase the cyclic carbonate conversion, it is preferable to feed in the aliphatic monohydric alcohol in an excess of at least 2 times the number of mols of the cyclic carbonate, but if the amount of the aliphatic monohydric alcohol used is too great, then it is necessary to make the apparatus larger. For such reasons, it is particularly preferable for the aliphatic monohydric alcohol to be used in an amount of 2 to 20 times the number of mols of the cyclic carbonate.

In the present invention, if carbon dioxide gas is present in the transesterification reactor in a high concentration, then the reaction rate for the transesterification reaction decreases. The reaction is thus generally carried out with the $CO_2$ concentration in the reaction liquid at not more than 500 ppm, preferably not more than 200 ppm, more preferably not more than 100 ppm.

Moreover, in the present invention, if water is present in the reaction liquid in the transesterification reactor in a high concentration, then hydrolysis of the cyclic carbonate proceeds at the same time as the transesterification reaction, and hence the dialkyl carbonate selectivity decreases. The reaction is thus generally carried out with the $H_2O$ concentration in the reaction liquid at not more than 200 ppm, preferably not more than 100 ppm.

In the present invention, if it is attempted to make the cyclic carbonate conversion in the transesterification reaction close to 100%, then the residence time increases and hence, as described above, it becomes impossible to obtain a high-purity diol, the required amount of the aliphatic monohydric alcohol becomes too high. Moreover, it is undesirable for the conversion to be too low, since then an apparatus for separating out and recovering unreacted cyclic carbonate becomes large. The transesterification reaction is thus generally carried out with the cyclic carbonate conversion in a range of from 95 to 99.999%, preferably from 98 to 99.99%, more preferably from 99 to 99.99%.

In the present invention, the dialkyl carbonate as one of the products is withdrawn from the transesterification reactor, generally being withdrawn from an upper portion of said reactor as a gaseous low boiling point component. The low boiling point component withdrawn from the upper portion of the reactor may comprise the dialkyl carbonate alone, or may be a mixture of the aliphatic monohydric alcohol and the dialkyl carbonate, and may contain a small amount of high boiling point products.

In the continuous multi-stage distillation column constituting the transesterification reactor, as an outlet from which the low boiling point component containing the dialkyl carbonate is withdrawn from said multi-stage distillation column, a gaseous material outlet is preferably provided between the starting material feeding position and the top of the column or at the top of the column, and is particularly preferably provided at the top of the column. So-called refluxing in which some of the low boiling point component withdrawn in this way is returned into the upper portion of said distillation column may also be carried out. If the reflux ratio is increased through this refluxing, then the efficiency of distillation of low boiling point products into the vapor phase is increased, and hence the low boiling point product concentration in the withdrawn gaseous component can be increased. However, it is undesirable to increase the reflux ratio too much, since then the required amount of thermal energy becomes high. The reflux ratio used is thus generally in a range of from 0 to 10, preferably from 0 to 5, more preferably from 0 to 3.

The low boiling point mixture withdrawn from the upper portion of the transesterification reactor can be fed into a dialkyl carbonate separating apparatus, and the dialkyl carbonate can be obtained by being withdrawn from the dialkyl carbonate separating apparatus. Examples of the dialkyl carbonate separating apparatus include a distillation separating apparatus, an extraction separating apparatus, a liquid-liquid extraction separating apparatus, a crystallization separating apparatus, an adsorption separating apparatus, a membrane separating apparatus, or the like. The separating apparatus may also be constituted from a plurality of such apparatuses of the same type, or a combination of a plurality of types of separating apparatuses may be used. Of the above separating apparatuses, it is particularly preferable to use the distillation separating apparatus.

In the case of using the distillation separating apparatus as said dialkyl carbonate separating apparatus, the low boiling point mixture withdrawn from the upper portion of the transesterification reactor is led into the distillation separating apparatus, where the components such as the dialkyl carbonate and the aliphatic monohydric alcohol contained in said reaction liquid or mixture can be separated out as a distillate or a column bottom liquid each comprising one of the components or a mixture thereof. Depending on the types of the starting materials, an azeotropic mixture may be obtained as a distillate or the column bottom liquid. After the reaction liquid or the low boiling point mixture withdrawn from the upper portion of the transesterification reactor has been separated into the distillate and the column bottom liquid by using the distillation separating apparatus in this way, the column bottom liquid or distillate containing the aliphatic monohydric alcohol can be fed back into the transesterification reactor.

As the distillation separating apparatus, a tray type multi-stage distillation column like the multi-stage distillation column used as the transesterification reactor may be used, or a packed column type distillation column packed with any of various packings may be used; such a column may be used alone, or a plurality may be used in combination. Here, the case that the aliphatic monohydric alcohol and the dialkyl carbonate are a combination forming a minimum boiling point azeotropic mixture is taken as an example in the following, specifically the case that methanol is used as the aliphatic monohydric alcohol and dimethyl carbonate will be explained. The low boiling point mixture withdrawn from the upper portion of the transesterification reactor containing methanol and dimethyl carbonate is continuously fed into the dimethyl carbonate separating column, a low boiling point component containing a minimum boiling point azeotropic mixture of methanol and dimethyl carbonate is continuously withdrawn from an upper portion of said dimethyl carbonate separating column, and dimethyl carbonate is continuously withdrawn from a lower portion of said dimethyl carbonate separating column, whereby dimethyl carbonate can be obtained.

Said dimethyl carbonate separating column is operated under a reduced pressure or an applied pressure, the operating pressure generally being in a range of from $0.5 \times 10^5$ to $50 \times 10^5$ Pa (0.51 to 51 kg/cm$^2$) in terms of the absolute pressure. The composition of the methanol/dimethyl carbonate minimum boiling point azeotropic mixture varies according to the operating pressure, and hence the operating pressure of said dimethyl carbonate separating column is selected to be an operating pressure such that dimethyl carbonate can be obtained from the lower portion of the column. That is, a pressure higher than the pressure corresponding to the methanol/dimethyl carbonate ratio in the material withdrawn from the upper portion of the transesterification reactor is selected.

The low boiling point component containing the minimum boiling point azeotropic mixture of methanol and dimethyl carbonate withdrawn from the upper portion of the dimethyl carbonate separating column can be fed into the transesterification reactor as starting material for the process of the present invention.

The upper portion of the continuous multi-stage distillation column in the present invention refers to a region from the top of said distillation column to a position at a height approximately ½ of the column height, and includes the top of the column. Moreover, the lower portion of the continuous multi-stage distillation column refers to a region from the bottom of said distillation column to a position at a height approximately ½ of the column height, and includes the bottom of the column.

The diol produced in the transesterification reactor is withdrawn from the lower portion of said reactor as a liquid high boiling point component. This high boiling point mixture contains the produced diol and unreacted cyclic carbonate, and may also contain the aliphatic monohydric alcohol, or the aliphatic monohydric alcohol and the dialkyl carbonate.

An outlet from which the liquid high boiling point mixture containing the produced diol is withdrawn from the transesterification reactor is provided in the lower portion of said reactor. Some of the reaction mixture withdrawn in this way may be heated using a reboiler and thus put into a gaseous form or a gas/liquid mixed form, and then returned into the lower portion of said reactor.

For the continuous multi-stage distillation column constituting the transesterification reactor, the liquid velocity and the gas velocity in said distillation column vary depending on the type of the trays used, but are generally made to be within a range such that flooding and weeping do not occur.

Some of the liquid high boiling point mixture withdrawn from the lower portion of the transesterification reactor may be fed back into the transesterification reactor so as to circulate unreacted cyclic carbonate and/or unreacted aliphatic monohydric alcohol back into said transesterification reactor.

When the high boiling point mixture containing the diol obtained as described above is subjected to separation in a diol purification step, generally, (1) in the case that the low boiling point component such as starting material aliphatic monohydric alcohol is contained, it is preferable to separate out said aliphatic monohydric alcohol or the like in advance using the separating apparatus such as a distillation apparatus and recycle the aliphatic monohydric alcohol back into the transesterification reactor, or (2) it is preferable for unreacted cyclic carbonate contained in said high boiling point mixture to be separated out in advance before feeding into the purification step. As the method of separating out the unreacted cyclic carbonate contained in said high boiling point mixture, there can be used, for example, (i) distillation separation, (ii) a method of converting into diol through hydrolysis, or (iii) a method of eliminating the unreacted cyclic carbonate through an ether producing reaction between the cyclic carbonate and the diol. It is particularly preferable to use the ether producing reaction.

That is, as a preferable separation method carried out on the high boiling point mixture withdrawn from the transesterification reactor before feeding into the diol purification step, two following methods can be used.

1. An example is a method in which, before the liquid high boiling point mixture withdrawn from the transesterification reactor is fed into the diol purification step, said liquid high boiling point mixture is continuously fed into a low boiling point component separating column comprising a continuous multi-stage distillation column having a side cut outlet provided in a lower portion thereof, a low boiling point component containing the dialkyl carbonate and the aliphatic monohydric alcohol remaining in said high boiling point mixture is continuously withdrawn from an upper portion of the low boiling point component separating column, a distillate containing the diol and the cyclic carbonate is withdrawn from the side cut outlet, and said low boiling point component withdrawn from the upper portion of the low boiling point component separating column is fed into the transesterification reactor and thus circulated back, while the distillate withdrawn from the side cut outlet of said low boiling point component separating column is fed into an ether producing reaction apparatus so as to carry out an ether producing reaction, before feeding into the diol purification step.

Examples of the low boiling point component separating column include a tray type multi-stage distillation column like the multi-stage distillation column used as the transesterification reactor, or a packed column type distillation column packed with any of various packings may be used.

2. An example is a method in which, before the liquid high boiling point mixture withdrawn from the transesterification reactor is fed into the diol purification step, said liquid high boiling point mixture is continuously fed into a low boiling point component separating column comprising a multi-stage distillation column, a low boiling point component containing the dialkyl carbonate and the aliphatic monohydric alcohol remaining in said high boiling point mixture is continuously withdrawn from an upper portion of the low boiling point component separating column, a high boiling point component containing the diol and the cyclic carbonate is withdrawn from a lower portion of said low boiling point component separating column and at this time an ether producing reaction is carried out in the lower portion of said low boiling point component separating column, and said low boiling point component withdrawn from the upper portion of the low boiling point component separating column is continuously fed into the transesterification reactor and thus circulated back, while the high boiling point component containing the diol and a produced ether withdrawn from the lower portion of said low boiling point component separating column is fed into the diol purification step.

When carrying out the above ether producing reaction, an ether producing reaction method described in Patent Document 20 (International Publication No. 00/51954) can be used, that is a method in which the mixture containing the produced diol and the unreacted cyclic carbonate is fed into an ether producing reaction apparatus, and the unreacted cyclic carbonate is subjected to an ether producing reaction with some of the produced diol, thus converting the unreacted cyclic carbonate into a straight chain ether represented by the following formula:

$$HO(R^1O)_nH$$

wherein $R^1$ is defined as above, whereby the amount of unreacted cyclic carbonate is reduced.

The reaction conditions in the ether producing reaction apparatus vary according to whether or not a catalyst is used, and the type and amount of the catalyst in the case that a catalyst is used, but the reaction temperature is generally in a range of from 50 to 350° C., preferably from 80 to 300° C., more preferably from 100 to 250° C. The reaction time varies according to whether or not a catalyst is used, the type and amount of the catalyst in the case that a catalyst is used, and the reaction temperature, but is generally in a range of from 0.001 to 50 hours in terms of the average residence time, preferably from 0.01 to 10 hours, more preferably from 0.02 to 5 hours. The reaction pressure also varies according to the reaction temperature used, but is generally in a range of from $1 \times 10^3$ to $2 \times 10^7$ Pa in terms of the absolute pressure, preferably from $1 \times 10^4$ to $1 \times 10^7$ Pa.

The cyclic carbonate conversion in the ether producing reaction is generally in a range of from 90 to 100%, preferably from 95 to 100%, more preferably from 98 to 100%.

Moreover, if carbon dioxide is introduced into the transesterification reactor, then the transesterification reaction is impeded, and hence the reaction rate decreases. It is thus preferable to separate out carbon dioxide withdrawn from the ether producing apparatus.

Furthermore, upon subjecting the reaction liquid containing the diol to separation using the distillation separation step as described in Patent Document 21 (Japanese Patent Application Laid-Open No. 2002-308804) or Patent Document 22 (Japanese Patent Application Laid-Open No. 2004-131394), a high-purity diol having a high UV transmittance and a low aldehyde content can be obtained even if a method in which water is fed into the distillation separation step is not used, although this method may of course be used at the same time.

In the present invention, it is not necessary to use a solvent, but with an objective of (1) facilitating the reaction operation, (2) obtaining the dialkyl carbonate and the diol efficiently by carrying out azeotropic distillation or extractive distillation, or the like, a suitable inert solvent such as ethers, aliphatic hydrocarbons, aromatic hydrocarbons, halogenated aliphatic hydrocarbons, or halogenated aromatic hydrocarbons may be used as a reaction solvent.

Moreover, as a substance that is inert in the reaction, an inert gas such as nitrogen, helium, argon or the like may be made to be present in the reaction system, and with an objective of speeding up the distilling off of low boiling point products produced, such an inert gas, or a low boiling point organic compound that is inert in the reaction, may be introduced in from the lower portion of the continuous multi-stage distillation column in a gaseous form.

EXAMPLES

Following is a detailed description of Examples of the present invention. However, the present invention is not limited to the following Examples.

In the following Examples, the selectivities for the ethylene glycol and the dimethyl carbonate are values based on the ethylene carbonate consumed, and the yields for the ethylene glycol and the dimethyl carbonate are values based on the ethylene carbonate put in. The position of each stage in the distillation column is represented by the number of that stage counting from the top of the column as the first stage. The aldehyde concentration was measured using a calorimetric method [(1) a suitable amount of the sample and 5 ml of an aqueous solution of 0.2% by weight of ferric chloride ($FeCl_3.6H_2O$) and 0.32% by weight of sulfamic acid were added to 50 ml of distilled water and uniform mixing was carried out, and then the mixture was left to stand for 1 hour; (2) 25 ml of the aqueous solution of 0.2% by weight of ferric chloride ($FeCl_3.6H_2O$) and 0.32% by weight of sulfamic acid was added, and distilled water was further added to make up to 100 ml; and (3) the absorbance at a wavelength of 635 nm was measured, and using a calibration curve produced with acetaldehyde as a reference substance, the concentration of aldehyde contained in the sample was determined as the acetaldehyde weight concentration converted value].

Example 1

Dimethyl carbonate (DMC) and ethylene glycol (EG) were produced continuously from ethylene carbonate (EC) and methanol (MeOH) using the apparatus shown in FIG. 1. EC was continuously fed in a liquid form from a conduit 2 via a preheater 3 at a flow rate of 200 g/h into the $3^{rd}$ stage of a continuous multi-stage distillation column 1 comprising an Oldershow distillation column having an inside diameter 4 cm and 40 stages, an ethylene glycol solution of 18% by weight of potassium hydroxide (KOH) (homogeneous catalyst) was continuously fed in a liquid form also into the $3^{rd}$ stage via a conduit 2' at a flow rate of 0.95 g/h, and a mixture of MeOH and DMC (weight ratio: MeOH/DMC=97/3) was continuously fed in a liquid form into the $20^{th}$ stage of the continuous multi-stage distillation column 1 from a conduit 5 via a preheater 6 at a flow rate of 636.4 g/h. The pressure at the top of the continuous multi-stage distillation column 1 was atmospheric pressure, and the temperature at the top of the column was 63.8° C. The temperature $T_1$ at the $21^{st}$ stage (the $19^{th}$ stage from the top of the total number of 38 stages in the tray portion in which the catalyst was present) was 80.5° C., the temperature $T_2$ in the column bottom portion was 98° C., the average residence time of the reaction liquid $\theta^1$ in the tray portion in which the catalyst was present was 2.4 hours, and the average residence time of the reaction liquid $O_2$ in the column bottom portion was 4.3 hours, the total average residence time thus being 6.7 hours. From these values, $\alpha+1.24\beta=2607$.

A gaseous low boiling point mixture distilled off from the top 4 of the column was condensed using a condenser 7, and some of the mixture was refluxed back into the top of the column via a conduit 8 (reflux ratio=0.4), while the remainder was fed as a column top withdrawn liquid (containing 67.9% by weight of MeOH and 32.1% by weight of DMC) at a flow rate of 695.4 g/h via a conduit 9 into a position 80 cm from the top of a DMC separating column 71 comprising a packed column type distillation column of inside diameter 2.5 cm and packed height 160 cm packed with Dixon packings (3φ) as packings.

Some of a column bottom liquid withdrawn via a conduit 11 from the bottom 10 of the continuous multi-stage distillation column 1 was heated in a reboiler 12 so as to supply energy required for the distillation thereto, and the remainder of the column bottom liquid was fed as a liquid high boiling point mixture [containing 70/65% by weight of EG, 29.16% by weight of MeOH, 0.08% by weight of EC, 0.02% by weight of DMC, 0.01% by weight of diethylene glycol (DEG) and other high boiling point impurities, and 0.08% by weight of KOH] at a flow rate of 200.2 g h via a conduit 14 into a position 100 cm from the top of a low boiling point component separating column 17 comprising a packed column type distillation column of inside diameter 2.5 cm and packed height 160 cm packed with Dixon packings (3φ) as packings.

The EC conversion for the transesterification reaction was 99.92%, the DMC selectivity was 99.9%, and the EG selectivity was 99.9%.

The DMC separating column 71 was operated at a column top pressure of $1.4 \times 10^6$ Pa, and a column bottom temperature of 205° C. A gaseous low boiling point mixture distilled off from the top 72 of the DMC separating column 71 was condensed using a condenser 75, and some of the mixture was refluxed back into the top of the column via a conduit 77 (reflux ratio=2), while the remainder was merged via a conduit 78 into the conduit 5, and fed into the continuous multi-stage distillation column 1 via the preheater 6. The composition of the liquid fed in from the conduit 5 was changed gradually from the MeOH/DMC mixture initially to MeOH only such that the composition fed into the continuous multi-stage distillation column 1 was kept constant.

Some of a column bottom liquid withdrawn via a conduit 79 from the bottom 73 of the DMC separating column 71 was heated in a reboiler 80 so as to supply energy required for the distillation thereto, and the remainder of the column bottom liquid was withdrawn via a conduit 82 at a flow rate of 204.3 g/h. The column bottom liquid was 99.9% by weight DMC.

The low boiling point component separating column 17 was operated at a column top pressure of atmospheric pressure, and a column bottom temperature of 201° C., thus carrying out an ether producing reaction between ethylene carbonate and ethylene glycol in the column bottom portion of the low boiling point component separating column 17, so as to convert into diethylene glycol (DEG). The residence time in the column bottom portion 26 of the low boiling point component separating column 17 was 1.5 hours. A gaseous component distilled off from the top of the low boiling point component separating column 17 was condensed using a condenser 19, and some of this component was refluxed back via a conduit 20, while the remainder was introduced via a conduit 21 into the top of a carbon dioxide-eliminating column 22. The reflux ratio was 1. Nitrogen gas was introduced into the column 22 from a conduit 23 provided at the bottom of the column 22, so as to carry out bubbling. Carbon dioxide-containing nitrogen gas was discharged from a conduit 24 provided at the top of the column 22. A carbon dioxide-eliminated liquid was circulated from the conduit 23 provided at the bottom of the column 22 at a flow rate of 58.3 g/h back into the $20^{th}$ stage of the continuous multi-stage distillation column 1.

A column bottom liquid from the low boiling point component separating column 17 was heated using a reboiler 28, and was withdrawn at a flow rate of 141.7 g/h from a conduit pipe 30 as an ether-produced reaction mixture [containing 99.74% by weight of EG, and 0.14% by weight of DEG and other high boiling point impurities; EC not detected].

The ether-produced reaction mixture was fed via the conduit 30 into a position 90 cm from the top of an EG purifying column 41 comprising a packed column type distillation column of inside diameter 2.5 cm and packed height 120 cm packed with Dixon packings (3φ) as packings.

The EG purifying column 41 was operated at a column top pressure of 4000 Pa (30 torr), and a column bottom temperature of 123.5° C. A liquid distillate was obtained as a side withdrawn liquid at a flow rate of 139.6 g/h from a conduit 56 provided in a position 50 cm from the top of the EG purifying column 41. Moreover, some of a column top distillate from the EG purifying column 41 was refluxed via a condenser 45 and a conduit 47 back into the top 42 of the EG purifying column 41, and the remainder was withdrawn from a conduit 48. The reflux ratio was 2. A column bottom liquid (containing 45.2% by weight of EG) was withdrawn from the bottom 43 of the EG purifying column 41, and some of this column bottom liquid was passed through a reboiler 50 and a conduit 51 and returned into the bottom 43 of the EG purifying column 41, while the remainder was withdrawn at 0.7 g/h via a conduit 52.

For the liquid EG withdrawn from the side-cut outlet of the EG purifying column, the amount of other organic components was below the detection limit (1 ppm for each component) according to gas chromatography, and the aldehyde concentration was measured using the colorimetric method to be 0.6 ppm. Moreover, the UV transmittance of this side withdrawn liquid at 220 nm was 89%. A polyester was produced taking this EG and dimethyl terephthalate as starting materials and using antimony as a catalyst. The polyester obtained had a high optical transmittance in the UV and visible regions. The above results show that for the system overall, the DMC yield was 99.8%, and very high-purity EG was obtained at a yield of 99.1%.

Example 2

DMC and EG were produced according to the same process as in Example 1, except that as the catalyst, instead of the homogeneous catalyst comprising an ethylene glycol solution of potassium hydroxide, there was used an anion exchange resin having quaternary ammonium groups as exchange groups (obtained by subjecting a Dowex MSA-1 Cl type to ion exchange with a 2N $Na_2CO_3$ aqueous solution, repeatedly washing with pure water, and then repeatedly washing with dry methanol, so as to carry out dehydration/drying, approximately 50% of the Cl⁻ ions being exchanged to $CO_3^{2-}$ ions), which was fixed to the $3^{rd}$ to $40^{th}$ stages of the tray portion (each approximately 5 vol % of the liquid residing portion) and the column bottom portion (approximately 10 vol % of the liquid residing portion) such as not to flow out. Here, the temperatures in the column were $T_1=80.4°$ C. and $T_2=98°$ C., and the average residence times of the reaction liquids were $\theta_1=2.2$ hours and $\theta_2=3.8$ hours, the total average residence time being 6.0 hours. From these values, $\alpha+1.24\beta=2460$. The EC conversion for the transesterification reaction was 99.9%, the DMC selectivity was 99.8%, and the EG selectivity was 99.8%.

Moreover, the amount of other organic components in the liquid EG withdrawn from the side-cut outlet of the EG purifying column according to gas chromatography was below the detection limit (1 ppm), the aldehyde concentration according to the colorimetric method was 0.8 ppm, and the UV transmittance at 220 nm was 88.5%. The DMC yield for the system overall was 99.7%, and the EG yield was 99.0%.

Comparative Example 1

DMC and EG were produced according to the same process as in Example 1, except that the continuous multi-stage distillation column 1 was made to be an Oldershow distillation column having an inside diameter 2.5 cm and 10 stages, and the stage into which the EC and the catalyst were fed was made to be the $1^{st}$ stage, while the stage into which the mixture of MeOH and DMC was fed was made to be the 5$^{th}$ stage. Here, the temperatures in the column were T$_1$ (5$^{th}$ stage)= 79.2° C. and T$_2$=95° C., and the average residence times of the reaction liquids were θ$_1$=0.18 hours and θ$_2$=0.25 hours, the total average residence time being 0.43 hours. From these values, α+1.24β=615. The EC conversion for the transesterification reaction was 91%, the DMC selectivity was 85%, and the EG selectivity was 83%.

Moreover, 1.8% of other organic components (mainly EC) was detected according to the gas chromatography analysis results on the liquid EG withdrawn from the side-cut outlet of the EG purifying column.

These results show that, because the residence time in the continuous multi-stage distillation column 1 was insufficient, the transesterification reaction results were poor.

Comparative Example 2

DMC and EG were produced according to the same process as in Example 1, except that the continuous multi-stage distillation column 1 was made to be an Oldershow distillation column having an inside diameter 6 cm and 80 stages, and the stage into which the EC and the catalyst were fed was made to be the 5$^{th}$ stage, while the stage into which the mixture of MeOH and DMC was fed was made to be the 40$^{th}$ stage. Here, the temperatures in the column were T$_1$ (42$^{nd}$ stage)=80.8° C. and T$_2$=97.5° C., and the average residence times of the reaction liquids were θ$_1$=10.8 hours and θ$_2$=21 hours, the total average residence time being 31.8 hours. From these values, α+1.24β=5853. The EC conversion for the transesterification reaction was 99.96%, the DMC selectivity was 99.1%, and the EG selectivity was 99.2%.

Moreover, the amount of other organic components in the liquid EG withdrawn from the side-cut outlet of the EG purifying column according to gas chromatography was 20 ppm, the aldehyde concentration according to the colorimetric method was 18 ppm, and the UV transmittance at 220 nm was 62%.

These results show that, because the residence time in the continuous multi-stage distillation column 1 was too long, aldehyde was produced in a large amount.

Example 3

DMC and EG were produced according to the same process as in Example 1, except that the continuous multi-stage distillation column 1 was made to be an Oldershow distillation column having an inside diameter 4 cm and 80 stages, and the stage into which the EC and the catalyst were fed was made to be the 5$^{th}$ stage, while the stage into which the mixture of MeOH and DMC was fed was made to be the 40$^{th}$ stage. Here, the temperatures in the column were T$_1$ (42$^{nd}$ stage)=80.8° C. and T$_2$=98° C., and the average residence times of the reaction liquids were θ$_1$=5.0 hours and θ$_2$=11.2 hours, the total average residence time being 16.2 hours. From these values, α+1.24β=4126. The EC conversion for the transesterification reaction was 99.95%, the DMC selectivity was 99.8%, and the EG selectivity was 99.8%.

Moreover, the amount of other organic components in the liquid EG withdrawn from the side-cut outlet of the EG purifying column according to gas chromatography was 2 ppm, the aldehyde concentration according to the colorimetric method was 1.6 ppm, and the UV transmittance at 220 nm was 87.5%. The DMC yield for the system overall was 99.7%, and the EG yield was 99.1%.

Comparative Example 3

DMC and EG were produced according to the same process as in Example 3, except that the continuous multi-stage distillation column 1 was made to be a pressurized column, and the column top pressure was made to be 6.4×10$^5$ Pa. Here, the temperature at the top of the column was 120.8° C., the temperatures in the column were T$_1$ (42$^{nd}$ stage)=132° C. and T$_2$=152° C., and the average residence times of the reaction liquids were θ$_1$=5.1 hours and θ$_2$=11.4 hours, the total average residence time being 16.5 hours. From these values, α+1.24β=5455. The EC conversion for the transesterification reaction was 99.97%, the DMC selectivity was 99.2%, and the EG selectivity was 99.1%.

Moreover, the amount of other organic components in the liquid EG withdrawn from the side-cut outlet of the EG purifying column according to gas chromatography was 16 ppm, the aldehyde concentration according to the colorimetric method was 14 ppm, and the UV transmittance at 220 nm was 65%.

Example 4

DMC and EG were produced according to the same process as in Example 1, except that the continuous multi-stage distillation column 1 was made to be an Oldershow distillation column having an inside diameter 2.5 cm and 30 stages, and the stage into which the EC and the catalyst were fed was made to be the 2$^{nd}$ stage, while the stage into which the mixture of MeOH and DMC was fed was made to be the 15$^{th}$ stage. Here, the temperatures in the column were T$_1$ (16$^{th}$ stage)=80.4° C. and T$_2$=98° C., and the average residence times of the reaction liquids were θ$_1$=0.5 hours and θ$_2$=0.62 hours, the total average residence time being 1.12 hours. From these values, α+1.24β=1022. The EC conversion for the transesterification reaction was 99.4%, the DMC selectivity was 99.3%, and the EG selectivity was 99.2%.

Moreover, the amount of other organic components in the liquid EG withdrawn from the side-cut outlet of the EG purifying column according to gas chromatography was below the detection limit (1 ppm), the aldehyde concentration according to the colorimetric method was 0.5 ppm, and the UV transmittance at 220 nm was 89%. The DMC yield for the system overall was 98.7%, and the EG yield was 97.9%.

Comparative Example 4

DMC and EG were produced according to the same process as in Example 4, except that the continuous multi-stage distillation column 1 was made to be a reduced pressure column, and the column top pressure was made to be 20,000 Pa (150 torr). Here, the temperature at the top of the column was 26.8° C., the temperatures in the column were T$_1$ (16$^{th}$ stage)=37.1° C. and T$_2$=49.8° C., and the average residence times of the reaction liquids were θ$_1$=0.49 hours and θ$_2$=0.6 hours, the total average residence time being 1.09 hours. From these values, α+1.24β=749. The EC conversion for the transesterification reaction was 92%, the DMC selectivity was 86%, and the EG selectivity was 85%.

Moreover, 1.6% of other organic components (mainly EC) was detected according to the gas chromatography analysis results on the liquid EG withdrawn from the side-cut outlet of the EG purifying column.

INDUSTRIAL APPLICABILITY

The present invention can be favorably used as a process enabling the dialkyl carbonate and the diol to be produced stably and conveniently, and enabling the high-purity diol to be produced with both the high conversion and the high selectivity.

We claim:

1. In a process for continuous production of a dialkyl carbonate and a diol, by continuously feeding a first starting material containing a cyclic carbonate as a main component thereof and a second starting material containing an aliphatic monohydric alcohol as a main component thereof into a tray column type continuous multi-stage distillation column, bringing the starting materials into contact with a catalyst present in said distillation column so as to bring about reaction in a tray portion and a column bottom portion, continuously withdrawing a low boiling point component containing a produced dialkyl carbonate from an upper portion of said distillation column, and continuously withdrawing a high boiling point component containing a produced diol from a lower portion of said distillation column, wherein the improvement comprises:

the following formula (1) being satisfied, $$780 \leq \alpha + 1.24 \times \beta \leq 5150 \quad (1),$$

wherein
$\alpha = \theta_1^{0.52} \times (T_1+120)^{1.2}$,
$\beta = \theta_2^{0.52} \times (T_2+120)^{1.2}$, $\theta_1$ (hours) is an average residence time of the reaction liquid in the tray portion of said distillation column in which the catalyst is present;

$T_1$ (° C.) is a temperature at a $(n/2)^{th}$ stage (a $((n+1)/2)^{th}$ stage in the case that n is odd) from the top of the tray portion in which the catalyst is present wherein n is a total number of stages therein;

$\theta_2$ (hours) is an average residence time of the reaction liquid in the column bottom portion of said distillation column; and $T_2$ (° C.) is a temperature in the column bottom portion.

2. The process for continuous production of the dialkyl carbonate and the diol according to claim 1, wherein the catalyst is a homogeneous catalyst.

3. The process for continuous production of the dialkyl carbonate and the diol according to claim 1 or 2, wherein $\theta_1$ is in a range of from 0.3 to 20 hours, and $\theta_2$ is in a range of from 0.3 to 25 hours.

4. The process for continuous production of the dialkyl carbonate and the diol according to claim 1, wherein each of $T_1$ and $T_2$ is in a range of from −20° C. to 350° C.

* * * * *